(12) United States Patent
Lévesque et al.

(10) Patent No.: US 7,663,749 B2
(45) Date of Patent: Feb. 16, 2010

(54) METHOD AND SYSTEM TO MEASURE THE CONCENTRATION OF CONSTITUENT ELEMENTS IN AN INHOMOGENEOUS MATERIAL USING LIBS

(75) Inventors: Marc Lévesque, Saint-Augustin-de-Desmaures (CA); Alain Cournoyer, Québec (CA)

(73) Assignee: Institut National D'Optique, Sainte-Foy (CA)

( * ) Notice: Subject to any disclaimer, the term of this patent is extended or adjusted under 35 U.S.C. 154(b) by 301 days.

(21) Appl. No.: 11/973,009

(22) Filed: Oct. 4, 2007

(65) Prior Publication Data
US 2009/0091745 A1    Apr. 9, 2009

(51) Int. Cl.
*G01N 21/63* (2006.01)

(52) U.S. Cl. .......................... 356/318; 356/72

(58) Field of Classification Search .................. 356/318
See application file for complete search history.

(56) References Cited

U.S. PATENT DOCUMENTS 6,466,309 B1 * 10/2002 Kossakovski et al. ......... 356/73

* cited by examiner

*Primary Examiner*—F. L Evans
(74) *Attorney, Agent, or Firm*—Ungaretti & Harris LLP

(57) ABSTRACT

A system and method to improve the accuracy of the measure of constituent element(s) in a sample containing domains potentially including the constituent element(s) are described herein. For each domain, the volume of the domain is estimated and the concentration of the constituent element(s) in the domain is determined using LIBS. When all the domains have been analyzed, the volumetric concentration of the domains is summed and divided by the total volume of the sample. Accordingly, by limiting the concentration analysis to separate domains, it is possible to improve the accuracy of the concentration analysis.

24 Claims, 6 Drawing Sheets

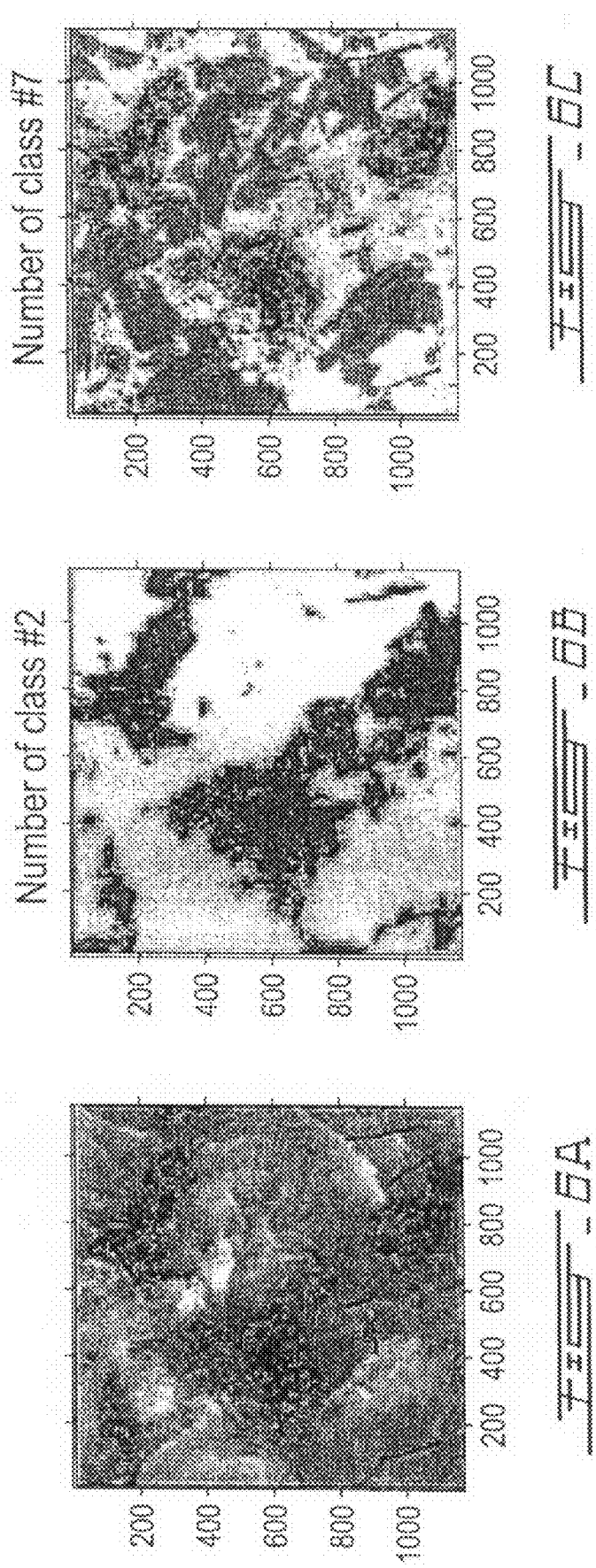

METHOD AND SYSTEM TO MEASURE THE CONCENTRATION OF CONSTITUENT ELEMENTS IN AN INHOMOGENEOUS MATERIAL USING LIBS

CROSS-REFERENCE TO RELATED APPLICATIONS

None.

FIELD OF INVENTION

The present invention generally relates to Laser-Induced Breakdown Spectroscopy (LIBS). More specifically, the present invention is concerned with a method and system to improve the precision of measured concentrations of constituent elements in inhomogeneous materials using LIBS.

BACKGROUND OF THE INVENTION

Quantitative and real time analysis of the elementary composition of materials is of great interest in many fields including geological survey, industrial production, environment diagnostics and on-line control of product quality, for example.

The LIBS technique is often used for the quick analysis of a sample's elementary constituents since it can be applied in situ and give results in real time.

While the LIBS technique is believed well known in the art, it will be summarized hereinbelow.

LIBS is a spark spectrochemical technique that uses a short-pulsed laser (nanoseconds) or an ultrashort pulse laser (picoseconds and femtoseconds) that is focused on a sample to create a microplasma near the surface thereof. The microplasma is a transient event having a peak temperature reaching 10,000 to 20,000 K.

In this environment, a portion of the sample is converted into plasma and the chemical bonds are broken to produce electronically excited atoms and ions. These excited species give off resonant and sharp radiation at specific wavelengths that depend on the constituent element.

By analysing the light emitted by the microplasma within a narrow range (generally from about 200 to about 980 nm) it is possible to identify the constituent elements by their specific emission wavelengths and to measure the concentration of the identified constituent elements by measuring the intensity of the light at their specific emission wavelengths.

LIBS may be considered a real-time procedure since its response time is generally less than a second.

The LIBS event generates a tremendous amount of data and, interestingly, virtually every laser shot produces a usable spectrum. Furthermore, LIBS is very good at analysing small particles.

LIBS can operate at atmospheric pressure while producing useful plasma emission intensities. The actual plasma emission is generally characterized both by a continuum spectrum (generally referred to as bremsstrahlung emission) and by discrete emission lines.

The continuum emission and the discrete emission, from both atoms and ions, decay at different rates. While the continuum emission decays usually within a few microseconds, the discrete emission persists strongly for tens of microseconds. The discrete plasma emission can, therefore, be resolved both spectrally and temporally to yield spectra containing the atomic emission lines corresponding to the atoms present in the plasma volume.

It is generally known that many variables can negatively influence the precision of LIBS measurements. Some of these variables such as the laser properties (wavelength, pulse duration, focusing spot size, etc.) and the detection window (delay time and gate width) can be taken into consideration when the measurements are taken. However, the physical properties of the sample are more difficult to take into account. This problem called "matrix effects" is well known in the art and is a factor that limits LIBS accuracy. Accordingly, the precision of LIBS measurement are generally relatively poor for many applications.

There is therefore a need for improvements in methods and systems for LIBS measurements.

BRIEF DESCRIPTION OF THE DRAWINGS

In the appended drawings:

FIGS. 6A-6C are images illustrating the analysis portion of the measuring method.

DETAILED DESCRIPTION

Figure 1:
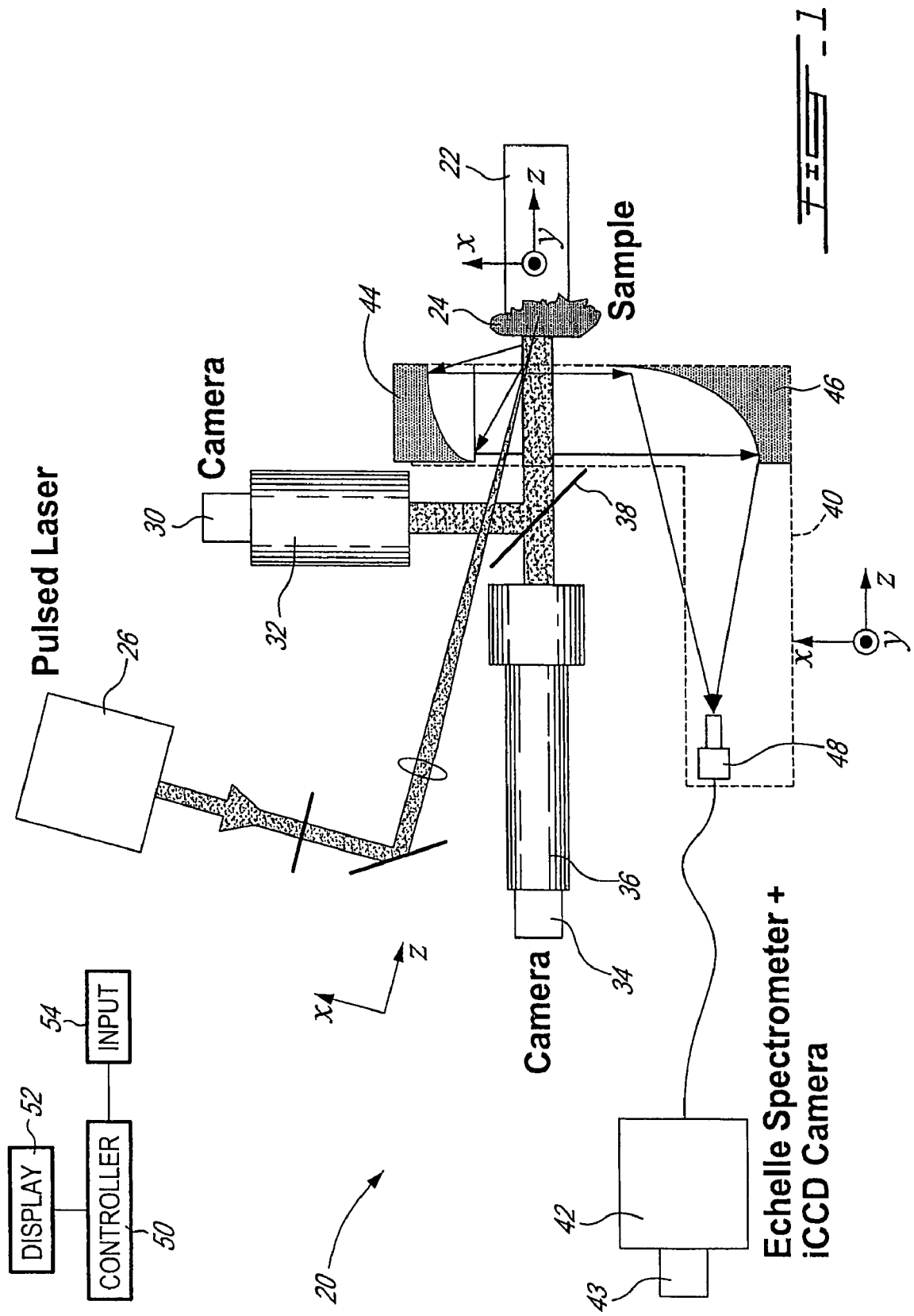
FIG. 1 is a schematic view of a concentration measuring system according to an illustrative embodiment of the present invention.

In accordance with an illustrative embodiment of the present invention, there is provided a method for measuring the concentration of a constituent element in an inhomogeneous sample having a relatively regular surface, the method comprising:

scanning at least a portion the relatively regular surface of the sample to obtain a plurality of pixels representing the surface;

grouping the pixels in a predetermined number of classes according to a pixel characteristic;

grouping contiguous pixels belonging to the same class into domains;

for each domain:
  determining the surface occupied by the domain;
  measuring, using LIBS, the concentration of the constituent element in at least one measurement site of the domain;
  determining the total quantity of the constituent element in the domain;

determining the concentration of the constituent element of the sample by dividing the added total quantity of the constituent element of each domain by the volume of the sample.

According to another illustrative aspect of the present invention, there is provided a method for measuring the concentration of a constituent element in an inhomogeneous sample having a relatively regular surface, the method comprising:

scanning at least a portion of the relatively regular surface of the sample to obtain a plurality of pixels representing the surface;

grouping contiguous pixels having the same pixel characteristic into domains;

grouping domains containing pixels having the same pixel characteristic into group of domains;

determining the surface occupied by each group of domains on the relatively regular surface;

selecting a portion of the scanned surface that includes at least one domain from each group of domains;

determining a measurement matrix having equidistant measurement sites covering the selected portion of the scanned image;

taking measurements, using LIBS, at every measurement sites;

determining, for each group of domains, the concentration of the constituent element in the group of domains by considering the LIBS measurements taken in measurement sites belonging to the group of domains;

determining the total quantity of constituent element of each group of domains;

determining the concentration of the constituent element of the sample by dividing the added total quantity of the constituent element of each group of domains by the volume of the sample.

According to another illustrative aspect of the present invention, there is provided a method for measuring the concentration of a constituent element in an inhomogeneous sample having a relatively regular surface, the method comprising:

determining the number, size and position of the domains on the relatively regular surface;

determining the surface occupied by each domain on the relatively regular surface;

for each domain, measuring, using LIBS, the concentration of the constituent element in at least one measurement site of the domain;

determining the total quantity of constituent element of each domain;

determining the concentration of the constituent element of the sample by dividing the added total quantity of the constituent element of each domain by the volume of the sample.

According to yet another illustrative aspect of the present invention, there is provided a system for measuring the concentration of a constituent element in an inhomogeneous sample having a relatively regular surface, the system comprising:

a controller;

a three-axis positioning assembly so configured as to hold the sample; the three-axis positioning assembly being controlled by the controller;

a pulsed laser generally aimed at the relatively regular surface of the sample, the pulse laser being controlled by the controller;

a camera generally aimed at the relatively regular surface of the sample; the camera being so configured as to supply a scanned image of at least a portion of the relatively regular surface to the controller;

a plasma emission collection assembly so configured as to collect light generated by a plasma on the relatively regular surface of the sample;

a spectrometer having an input so configured as to receive the light collected by the plasma emission collection assembly; the spectrometer having an output; the spectrometer being controlled by the controller;

an iCCD camera so mounted to the output of the spectrometer as to receive an image therefrom; the iCCD camera being so configured as to supply the image to the controller;

wherein the controller may control the three-axis positioning assembly so as to place a desired measurement site at the aimed position of the pulse laser, control the pulsed laser as to generate a laser pulse that generates a plasma at the desired measurement site, receive the spectrum from the iCCD camera and determine the concentration of the constituent element from the received spectrum; the controller being further configured as to make such measurements at predetermined measurement sites determined by examination of the scanned image and to calculate the total concentration of the constituent element from the determined concentrations of the constituent element at the predetermined measurement sites.

It is to be noted that the term "domain" is to be construed, herein and in the appended claims, as any finite three-dimensional portion of a body that is statistically homogeneous on the scale of the domain.

It is also to be noted that the expression "inhomogeneous material" is to be construed, herein and in the appended claims, as any solid material that contains at least one domain of generally homogeneous material that is different from other portions of the solid material.

It is also to be noted that the term "sample" is to be construed, herein and in the appended claims, as the volume of material for which a measurements are actually taken.

It is also to be noted that the present description refers to different documents. These documents are hereby included herein by reference.

Other objects, advantages and features of the present invention will become more apparent upon reading of the following non-restrictive description of illustrative embodiments thereof, given by way of example only with reference to the accompanying drawings.

Generally stated, illustrative embodiments of the present invention concern a system and method to improve the accuracy of the measurement of constituent elements in a sample containing discrete domains of homogeneous material potentially including the constituent elements. In specific embodiments of the present invention, each domain is considered as being part of a group determined according to characteristics of the domain. For each group, the concentration of the constituent elements is determined using LIBS. When all the groups of the sample have been analyzed, the quantity of the constituent elements of the groups is summed and divided by the total volume of the sample to yield the concentration of the constituent elements in the sample. Accordingly, by limiting the concentration analysis to various discrete domains of the sample, it is possible to improve the accuracy of the concentration analysis.

Turning now to FIG. 1 of the appended drawings a LIBS system 20 for the determination of the concentration of the constituents of a sample according to an illustrative embodiment of the invention will be described.

The LIBS system 20 includes a three-axis positioning assembly 22 designed to removably hold a sample 24, a pulsed laser 26 which is generally aimed at the sample 24, a first camera 30 provided with a 0.25 zoom 32, a second camera 34 provided with a 4× zoom 36. Both cameras 30 and 34 are aimed at the sample 24 via a 50/50 beamsplitter 38. The LIBS system 20 also includes a plasma emission collection assembly 40 supplying light generated by plasma to a spectrometer 42 provided with an iCCD (intensified Charged-Coupled-Device) camera 43 at its output.

The three-axis positioning assembly 22, the laser 26, the cameras 30 and 34 and the spectrometer 42 are controlled by a controller 50 provided with a display 52 and an input device 54. For clarity purpose, the interconnections between these various elements and the controller 50 have not been illustrated in FIG. 1.

The three-axis positioning assembly 22 is so controlled by the controller 50 that it may position a desired portion of the sample 24 in the line of sight of the pulsed laser 26 for scanning reasons or for LIBS measurement reasons as will be described hereinbelow. As a non-limiting example, it has been found that a three-axis positioning assembly manufactured by Physik Instrumente model M-126.DG is adequate for the present application.

The pulsed laser 26 is used to create a plasma for LIBS measurement as is generally known in the art.

The pulsed laser 26 may be a short pulse laser (nanoseconds) or an ultrashort pulse laser (femtoseconds and picoseconds). It has been found advantageous to use a ultrashort pulse laser for many reasons:

The plasma generated is more reproducible and the resonant and sharp radiation at specific wavelengths that depend on the constituent element is more stable, improving the precision and the sensitivity of the measure;
   Since there is less power involved in the plasma, the size of the plasma is decreased, which limits the effects of optical self-absorption of the plasma to thereby improve the precision of the concentration measurement;
   The emission continuum is weaker and decreases more rapidly;
   Since it is less of a thermal reaction, the "matrix effects" are decreased which leads to increase precision;
   Since the heat-affected zone is smaller, it is possible to take LIBS measurement closer to one another; and,
   It can be applied to more material since it is less sensitive to the nature of the material.

As a non limiting example, it has been found that the ultrashort pulsed laser manufactured by Quantronix under model Integra C 1.0 is adequate to be used as the pulsed laser 26.

The camera 30, provided with a 0.25× zoom 32 is used to scan the prepared surface of the sample 24 as will be described hereinbelow. The controller 50 therefore controls the camera 30 and the positioning assembly 22 accordingly. The data from the camera 30 is transferred to the controller 50 and may be displayed on the display 52. The camera 30 may be a monochrome, a color or a hyperspectral camera. As a non limiting example, it has been found that the camera 30 could be a CCD camera manufactured by Sony under model number DFW-SX910. It is to be noted that other types of camera could be used.

The camera 34, provided with a 4× zoom 36, is used to ensure that the correct location, as determined by the controller 50 or by the user, is aimed at by the pulsed laser 26 for the LIBS measurement as will be described hereinbelow. The camera 34 is similar to the camera 30.

The plasma emission collection assembly 40 is designed to transmit the light generated by the pulsed laser 26 emission onto the sample 24 to the spectrometer 42. The collection assembly 40 should be as efficient as possible in the entire spectrum considered while being substantially free of chromatic aberration. It is well known that reflective optics is well suited to this task. The plasma emission collection assembly 40 includes two parabolic mirrors 44 and 46 and a UV/VIS (Ultraviolet-Visible) optic fiber 48 connecting the collection assembly 40 to the spectrometer 42. The parabolic mirrors 44 and 46 are mounted off-axis. The mirror 44 collects the light emitted by the plasma created on the sample by the laser 26 and the mirror 46 focalizes the collected light onto the optic fiber 48. To adequately position the plasma emission collection assembly 40, a three axis positioning assembly (not shown) is provided. It is therefore possible to move the collection assembly depending on the position of the plasma that the user desires to measure. Of course, the three axis positioning assembly may be connected to the controller 50 to be controlled thereby.

As a non limiting example, it has been found that the parabolic mirrors manufactured by Edmund under model number M47-087 are adequate to be used as the mirrors 44 and 46 and that the UV/VIS optic fiber supplied by Ocean Optics under model number QP50-2-UV-VIS is adequate to be used as the optic fiber 48.

The spectrometer 42 is used to make the LIBS measurements and it receives the plasma generated light from the optic fiber 48. To improve accuracy, it is interesting to use a spectrometer that has a wide bandwidth so as to acquire the entire spectrum of elements at the same time. Accordingly an Echelle spectrometer is interesting. While many spectrometers can be used, it has been found that the spectrometer manufactured by Andor under model number Mechelle 5000 is adequate to be used as the spectrometer 42.

The iCCD camera 43 is mounted to the output of the spectrometer 42. It is interesting to use time-gating to delay the beginning of the signal acquisition and to circumscribe an acquisition window to thereby limit the influence of the emission continuum which decreases with time. It is however to be noted that the use of an ultra-short pulse laser as the ablation source creates an emission continuum that influences less the LIBS measurements. Accordingly, the time-gating might be optional and the iCCD camera 43 could be replaced by a conventional camera (not shown).

Figure 2:
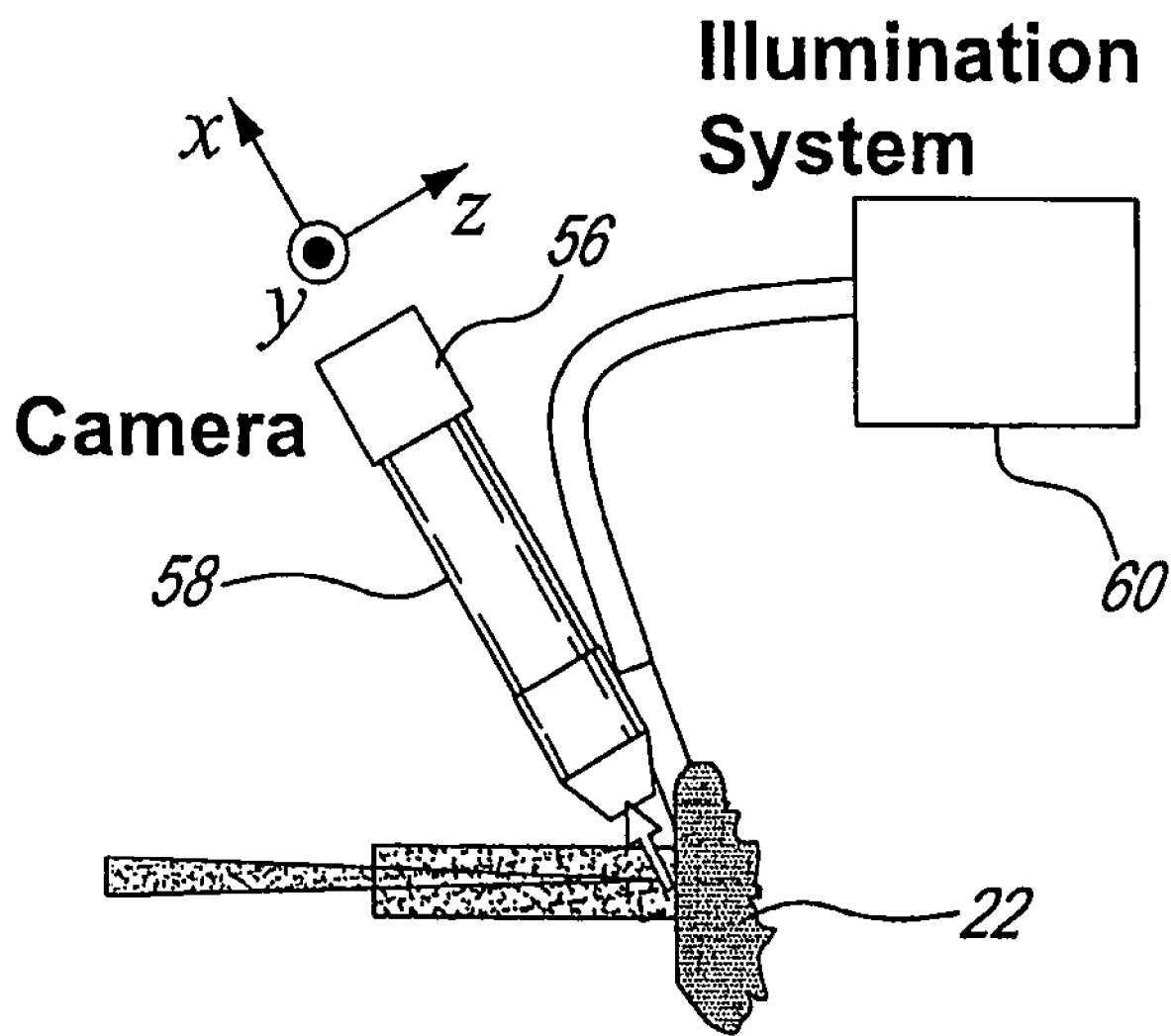
FIG. 2 is a schematic side view of a portion of the concentration measuring system of FIG. 1.

As can be better seen from FIG. 2, which is a side view of a portion of the system 20 of FIG. 1, the system 20 also includes a camera 56 provided with a 10× zoom 58 and an illumination assembly 60. The camera 56 is used to obtain an image of the plasma generated on the sample 24 and to supply this image to the controller 50 to allow the controller to localize the plasma, determine the dimensions, shape and other characteristics of the plasma and to obtain an energy density profile thereof. To do this, the camera 56 is synchronized with the pulse laser 26. The camera 56 may be a monochrome or color camera and is mounted away from the plasma to limit the number of elements in the proximity of the sample and to protect the lens from the generated plasma. The data obtained is used to optimize the system 20 set-up, for example by calibrating the positioning assembly 22 and by helping during the alignment of the different optical elements.

The camera 56 is mounted to a three-axis positioning assembly (not shown) to allow the adequate positioning and focus of the camera with respect to the plasma. Of course, the three-axis positioning assembly may be connected to the controller 50 to be controlled thereby.

It is to be noted that the relative energy density emitted by the plasma gives an approximation of the temperature of the plasma and that the dimensions of the plasma gives an approximation of the weight of the matter that is ablated by the plasma. These data could optionally be used to normalize the emission spectrum of the plasma to allow the correction of the LIBS measurement characteristics between laser pulses.

It is to be noted that the use of the camera 56 is optional should it be only used to determine the size of the plasma and to optimize the set-up system 20. Indeed, this information could be determined during a set-up phase of the system 20 and not be required afterwards.

It has been found that a CCD camera manufactured by Pixelink under model number PL-B781F is adequate to be used as the camera 56. Of course, other types of camera could be used.

The controller 50 may be a computer provided with an adequate acquisition card.

Generally stated, methods according to illustrative embodiments of the present invention are concerned with the measurement of the concentration of constituent element(s) in discrete domains and, by estimating or measuring the volume of the discrete domains in the sample, determining the concentration of the constituent element(s) for the entire sample.

Figure 3:
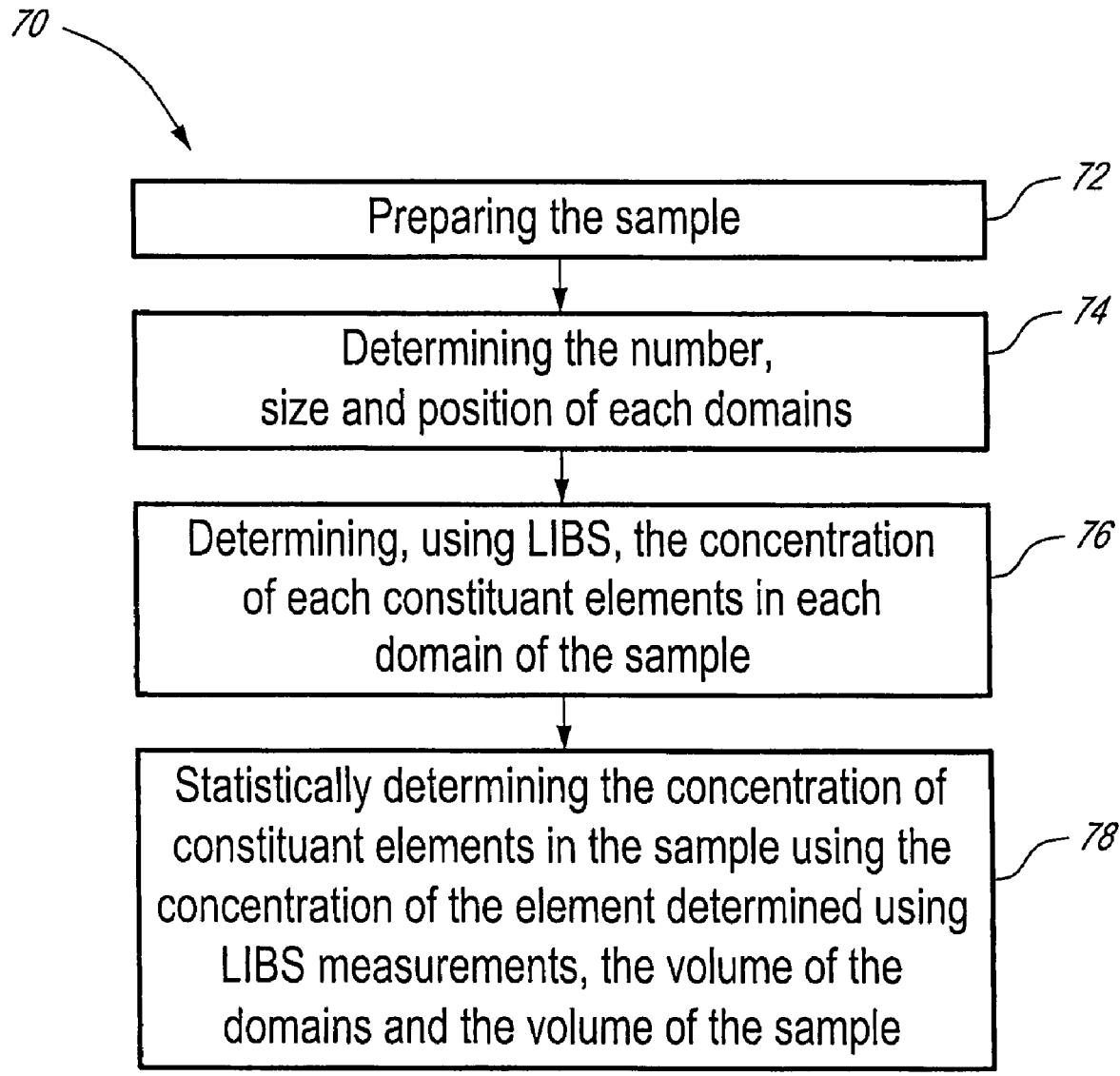
FIG. 3 is a block diagram of a first illustrative method for measuring the concentration of a constituent element according to an aspect of the present invention.

Turning now to FIG. 3 of the appended drawings, a LIBS measurement method 70 according to an illustrative embodiment of an aspect of the present invention will be described.

The first step 72 of the method 70 generally consists in preparing the sample. The sample 24 may be, for example, a surface rock or a core sample. The preparation of the sample 24 includes the creation of a regular surface thereon and the polishing of this surface. This regular surface will be preferably flat or cylindrical. For example, a diamond saw can be use to create the regular surface and emery paper can be used to polish the regular surface to yield a prepared surface.

The determination of the size and position of the various domains present on the prepared surface is done in step 74. As mentioned hereinabove, a domain is a portion of the sample that is contiguous and has a homogeneous composition of components. This determination can be done manually, for example by a geologist using a scanned image of the surface where the domains are manually selected so as to cover the entire surface of the prepared surface. It is to be noted that the domains are so determined that any point on the prepared surface is part of a single domain.

Next, in step 76, the concentration of the constituent elements is determined, using LIBS, for each domain determined in step 74.

It is to be noted that many LIBS technique can be used to make the LIBS measurement. For example, a Calibration Free LIBS (CF-LIBS) technique developed by Ciucci et al. ["New procedure for quantitative elemental analysis by laser-induced plasma spectroscopy", Applied Spectroscopy, vol 53, no 8, 1999, pp. 960-964] can be used.

Once all the LIBS measurements have been taken and the concentration results for each domain determined in step 74 are determined by the controller, the method 70 then statistically determines the concentration of the constituent elements for the entire sample in step 78.

To achieve this, the volume occupied by each domain must be determined. First, the surface area of each domain is first determined, for example by using a scanned image. Since the LIBS technique is generally a surface technique, i.e. creating craters having depth that range from about 1 to about 100 micrometers, it may be considered that the boundaries of each domain are perpendicular to the prepared surface of the sample for these small depths. Accordingly, the volume occupied by a domain may be determined as follows:

$$Volume_{Domain} = Surface_{Domain} * \sigma$$

Where $\sigma$ is a predetermined thickness in the micrometer range.

The total volume of the sample for further calculations is determined as follows:

$$Volume_{Sample} = Surface_{Sample} * \sigma$$

Accordingly, the total concentration for the entire sample is given by:

$$Concentration_{Sample} = \frac{\sum_{Domain}(Volume_{Domain} \times Concentration_{Domain})}{Volume_{Sample}}$$

Where $Concentration_{Domain}$ is the concentration of a constituent element in a particular domain. In other words, the quantity of the constituent element in each domain is calculated and summed and the result is divided by the volume of the sample to yield the concentration of the constituent element in the sample.

Figure 4:
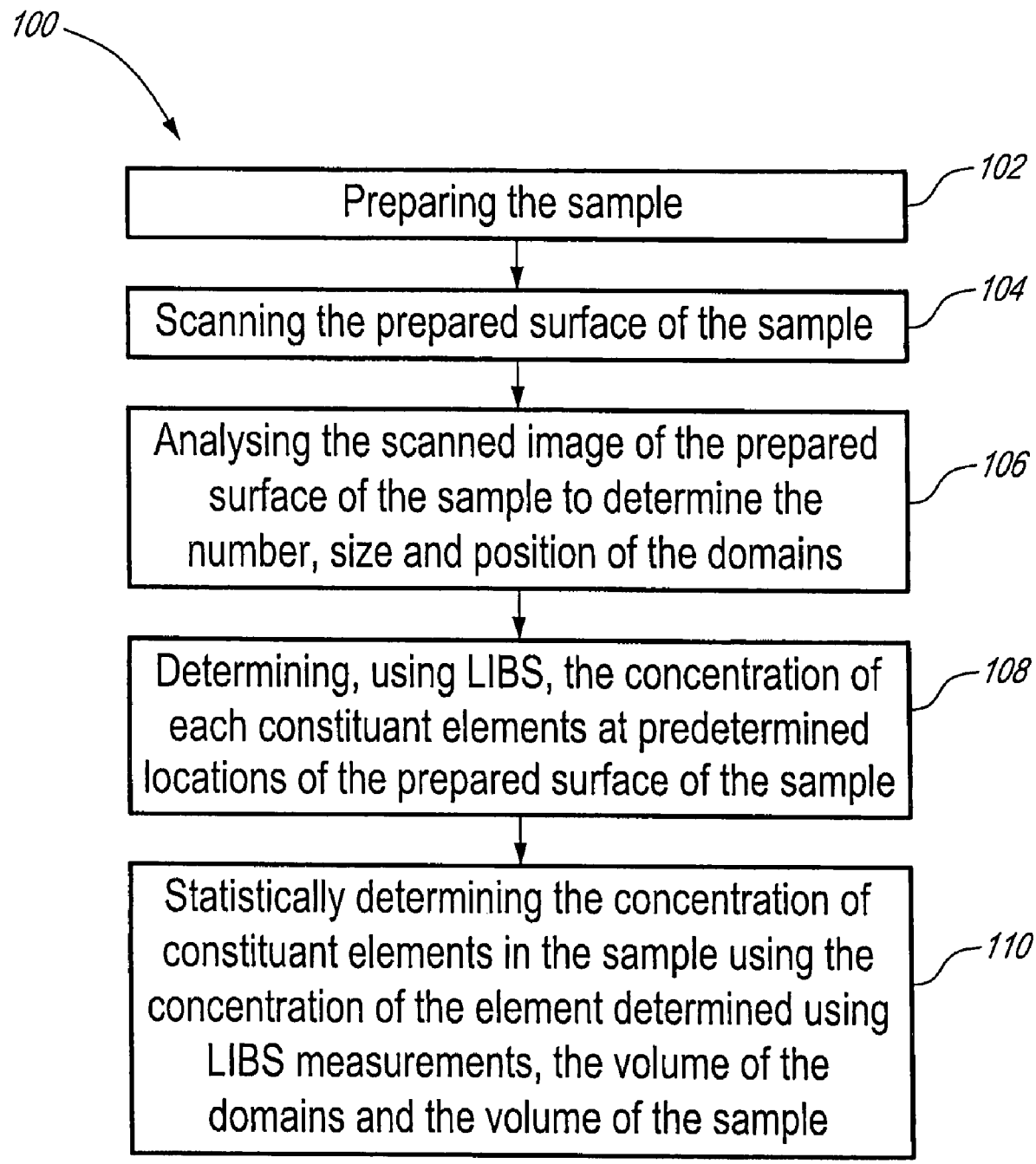
FIG. 4 is a block diagram of a second illustrative method for measuring the concentration of a constituent element according to an aspect of the present invention.

Turning now to FIG. 4 of the appended drawings, a LIBS measurement method 100 according to an illustrative embodiment of an aspect of the present invention will be described. It is to be noted that while the method 100 will be described with reference to the elements of the system 20 illustrated in FIGS. 1 and 2, other systems (not shown) could be designed or assembled to carry out this illustrative method 100.

The first step 102 is similar to the sample preparing step 72 described hereinabove and generally consists in preparing the sample for LIBS. Again, the sample 24 may be, for example, a surface rock or a core sample.

Once the prepared surface is ready, the sample 24 may be mounted to the three-axis positioning assembly 22 so that the prepared surface faces the camera 34.

The next step 102 is to scan an image of at least a portion of the prepared surface of the sample 24 via the camera 30. If a small enough portion of the surface is to be scanned, it can be done without displacement of the three-axis positioning assembly 22 and sent to the controller 50. If a larger portion of the prepared surface has to be scanned, multiple contiguous images of the surface can be obtained by the camera 30 while the three-axis positioning assembly 22 is moved by the controller 50. The controller 50 may then assemble the multiple images according to known techniques to obtain an image of the desired portion of the prepared surface. FIG. 6A illustrates a grey-level scan of a portion of a sample.

The scanned image of the prepared surface is then analyzed in step 106 to determine the number, size and position of the discrete domains. As mentioned hereinabove, a domain is a portion of the sample that is contiguous and has a generally homogeneous composition of components. It has been assumed herein that a finite contiguous portion of the surface that appears homogeneous on the scanned image is made of a composition of elements that is also homogeneous and therefore constitutes a domain.

Accordingly, according to known image analysis techniques, the analysis of the scanned image includes the grouping of pixels of this image that are generally homogeneous and contiguous into domains. Since there is a large number of possible grey levels that a pixel may take, all the pixels of the scanned image are divided among a given number of "classes". Pixels of the same class are considered to have similar characteristics. When pixels of the same class are contiguous and create a finite portion of the image, they define a domain. If many different domains are made of pixels that belong to the same class, these domains are considered from the same domain group and the composition of those domains may be considered to be the same.

FIG. 6B illustrates the analysis of the scanned image of FIG. 6A when the given number of classes used in the image analysis is two (2). As can be seen from the comparison of FIGS. 6A and 6B, many pixels that appear different to the human eye have been considered in the same class by the image analysis.

In sharp contrast, FIG. 6C illustrates the analysis of the same scanned image of FIG. 6A when the given number of classes is seven (7). As can be seen from this figure, the variations of the appearance of the pixels in the scanned image are well reproduced in the analyzed image.

It is also to be noted that the scanned image analysis can be done solely by the controller running an appropriate program or can be done by the controller in collaboration with an operator having geological experience. For example, supervised classification using the Hidden Markov Model could be used. The Hidden Markov Model is explained in "Hidden Markov Models: Estimation and Control (Stochastic Modelling and Applied Probability)", Robert J. Elliot et al., Publisher: Springer; 1 edition (Jan. 9, 1997), ISBN-10: 0387943641, ISBN-13: 978-0387943640.

Alternatively, the scan image analysis could be done solely by an operator.

Of course, while the description of the scanned image analysis hereinabove is concerned with the grey level as a means to determine the visual homogeneity of pixels, and thereby determine the class to which each pixel belongs to, other features such as the intensity, the color or the fluorescence of the pixel could be used, depending on the technology used for the camera 30. Of course, other features of the pixel could be used.

Once the number, size and position of the domains are obtained, the LIBS measurement (step 108) may take place. For each group of domains, i.e. domains having material that have the same characteristics, one could decide a) to take one LIBS measurement in a domain of the group, b) to take many measurement in one particular domain of this group to determine mean concentration values for this class, c) to take many measurements from different domains of this group to determine mean concentration values for this class, d) to take a measurement for each domain of this group to determine mean concentration values for this class. The precision of the results and the speed at which results must be obtain dictate the number of measurements to be taken.

For each LIBS measurement, the three-axis positioning system 22 positions the desired portion of the sample in the correct position for the creation of the plasma in the domain of interest.

Once the correct positioning is confirmed by the camera 34, the pulsed laser 26 generates the plasma and the light collected by the collection system 40 is transferred to the spectrometer 42 and the iCCD camera 43 supplies this data to the controller 50.

Again, it is to be noted that many LIBS technique can be used to make the LIBS measurement. For example, a Calibration Free LIBS (CF-LIBS) technique developed by Ciucci et al. ["New procedure for quantitative elemental analysis by laser-induced plasma spectroscopy", Applied Spectroscopy, vol 53, no 8, 1999, pp. 960-964] can be used.

One skilled in the art will understand that the LIBS measurements, including the correct positioning of the sample prior to the plasma generation, may be automated by the controller 50.

Once all the LIBS measurements have been taken and the concentration results for each group of domains are determined by the controller, the method 100 then statistically determines the concentration of the constituent elements for the entire sample in step 110.

To achieve this, the volume occupied by each group of domains must be determined. First, the surface area of each group is first determined using the scanned image as analyzed in step 106. More specifically, the surfaces of the domains of a particular group are added. Since the LIBS technique is generally a surface technique, i.e. creating craters having depth that range from about 1 to about 100 micrometers, it may be considered that the boundaries of each domain are perpendicular to the prepared surface of the sample for these small depths. Accordingly, the volume occupied by a group of domains may be determined as follows:

$$Volume_{Group} = Surface_{Group} * \sigma$$

Where $\sigma$ is a predetermined thickness in the micrometer range.

The total volume of the sample for further calculations is determined as follows:

$$Volume_{Sample} = Surface_{Sample} * \sigma$$

Accordingly, the total concentration of an element for the entire sample is given by:

$$Concentration_{Sample} = \frac{\sum_{Group}(Volume_{Group} \times Concentration_{Group})}{Volume_{Sample}}$$

Where $Concentration_{Group}$ is the concentration of a constituent element in the particular group. In other words, the quantity of the constituent element in each group is calculated and summed and the result is divided by the volume of the sample to yield the concentration of the constituent element in the sample.

As mentioned hereinabove, the $Concentration_{group}$ value may be determined by a single LIBS measurement of a particular domain of a group or by many LIBS measurements of the same or different domains of the group. If, for example, all the domains of a group are sampled to obtain a mean value of the concentration, the following equation may be used:

$$Concentration_{Group} = \frac{\sum_{domains}(Volume_{domain} \times Concentration_{domain})}{Volume_{Group}}$$

Figure 5:
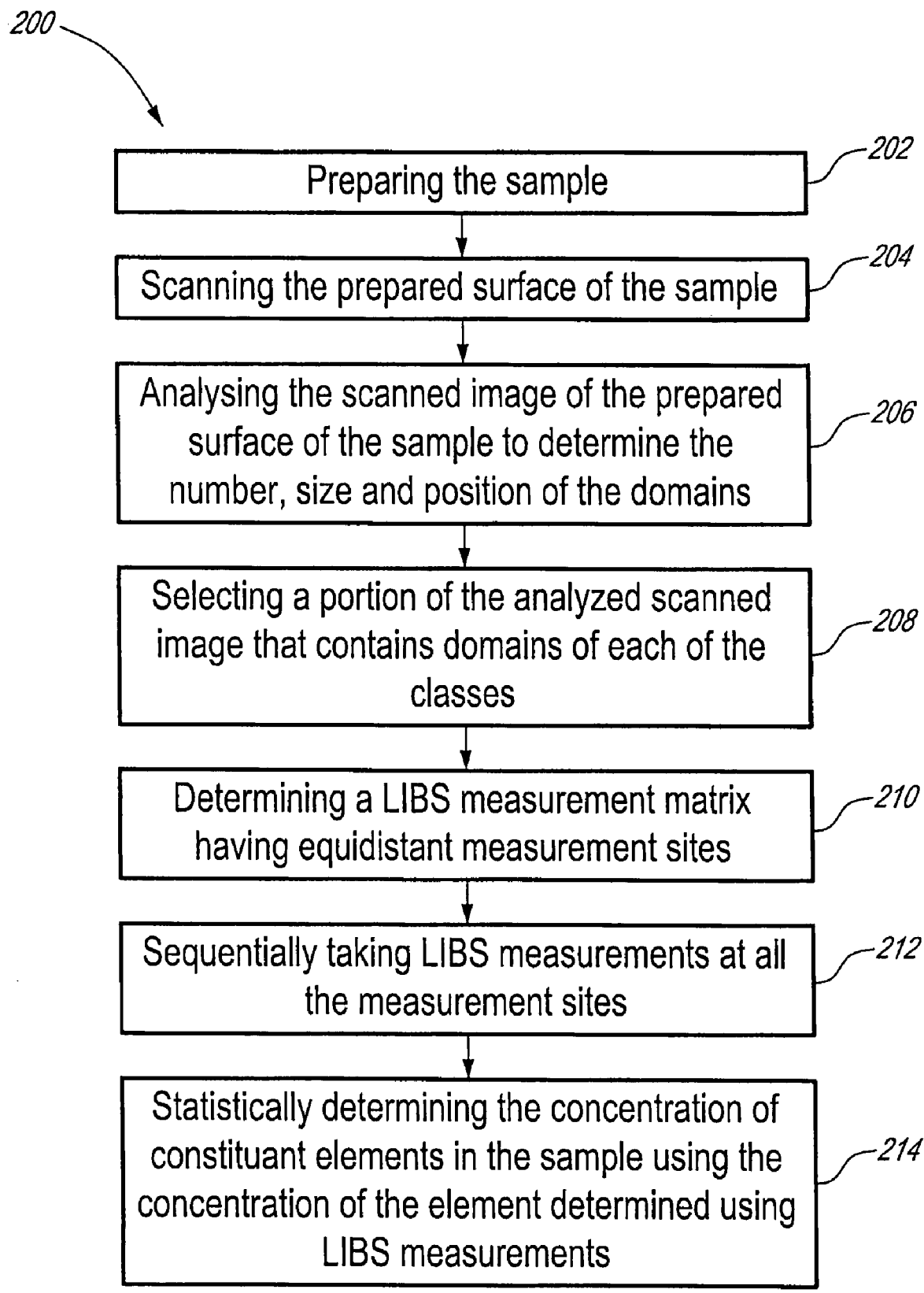
FIG. 5 is a block diagram of a third illustrative method for measuring the concentration of a constituent element according to an aspect of the present invention.

Turning now to FIG. 5 of the appended drawings, a method 200 according to another illustrative embodiment of the present invention will be described. It is to be noted that since some of the steps are identical to the steps of the method 100 described hereinabove, only the different steps will be described hereinbelow.

The surface of the sample is prepared (step 202), scanned (step 204) and analyzed to determine the number size and position of the domains (step 206) as it is done in the method 100.

Then, at step 208, a portion of the analyzed scanned image is selected. This section advantageously contains at least one domain of each group of domains present in the sample.

A LIBS measurement matrix is then determined in step 210. This matrix defines equidistant measurement sites. The distance between the measurement sites is such that each domain contained in the selected portion includes a measurement site.

Step 212 consists in sequentially taking LIBS measurements at every measurement sites defined in step 210. It is to be noted that this can be done automatically via the controller that controls the three-axis positioning system.

To determine the concentration of the constituent elements in the selected portion of the sample, the controller determines to which domain, therefore to which group of domains, each LIBS measurement belongs. Then, the concentration calculation may take place as described hereinabove in step 110 where the selected portion of the sample is considered the entire sample.

The results thus obtained for the selected portion may then be extended to the entire scanned surface of the sample.

It is also possible, in step 214 to obtain the concentration of the constituent element separately for each group of domains and to then generalize the results for the entire sample surface.

The use of systems and methods according to illustrative embodiments of the present invention has many advantages, such as:

In the geological survey for the mining industry, it is possible to obtain more accurate results, particularly when the concentration of the constituent element is low and contained in a few domains since only a small number of localized LIBS measurements are then taken;

It is possible to analyze simultaneously all the elements of the periodic chart; and The technique does not require a complicated sample preparation procedure.

Many modifications can optionally be done to the system and method to reinforce the LIBS signal to thereby improve the sensibility of the LIBS measurement.

Example of these Modifications Include:

Placing the sample in an Argon gas environment;

Reducing the gas pressure in the vicinity of the sample;

Configuring the pulsed laser so as to generate two pulses at very close intervals (microseconds); the first laser pulse causes a shockwave that reduces the gas pressure at the plasma site and the second laser pulse can therefore generate a more intense plasma in the lower pressure atmosphere;

Using microwaves to increase the temperature at the plasma site;

Configuring the pulse laser so as to generate two pulses at extremely close intervals (hundreds of picoseconds); the temperature of the plasma is then higher since the second pulse heats the plasma produced by the first laser pulse It is to be noted that the above mentioned modifications are not required to obtain good concentration results. It is also to be noted that the sample and the three-axis positioning assembly should be somehow enclosed should one decide to provide an argon or low pressure atmosphere.

One skilled in the art will understand that while the above description of illustrative embodiments of the present invention has been described hereinabove in a geological survey environment, this should not be construed as to limit the present invention. Indeed, industrial production, environment diagnostics and on-line control of product quality, for example, could benefit from embodiments of the present invention.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

What is claimed is:

1. A method for measuring the concentration of a constituent element in an inhomogeneous sample having a relatively regular surface, the method comprising:

scanning at least a portion of the relatively regular surface of the sample to obtain a plurality of pixels representing the surface;

grouping the pixels in a predetermined number of classes according to a pixel characteristic;

grouping contiguous pixels belonging to the same class into domains; and, for each domain:

determining the surface occupied by the domain;

measuring, using LIBS, the concentration of the constituent element in at least one measurement site of the domain;

determining a total quantity of the constituent element in the domain; and, determining a concentration of the constituent element of the sample by dividing an added total quantity of the constituent element of each domain by a volume of the sample.

2. The concentration measurement method of claim 1, wherein the pixel characteristic is selected from the group consisting of shade of grey, color, fluorescence and intensity.

3. The concentration measurement method of claim 1, wherein the regular surface is selected from the group consisting of a flat surface and a cylindrical surface.

4. The concentration measurement method of claim 1, wherein the concentration of the constituent element in the sample is determined by:

$$Concentration_{Sample} = \frac{\sum_{Domains}\left(\begin{array}{c}Volume_{Domain} \times \\ Concentration_{Domain}\end{array}\right)}{Volume_{Sample}}$$

where $Volume_{Sample} = Surface_{Sample} * \sigma$ $Volume_{Domain} = Surface_{Domain} * \sigma$ σ being a thickness so determined that the boundary of each domain may be assumed perpendicular to the relatively regular surface of the sample.

5. A method for measuring the concentration of a constituent element in an inhomogeneous sample having a relatively regular surface, the method comprising:

scanning at least a portion of the relatively regular surface of the sample to obtain a plurality of pixels representing the surface;

grouping contiguous pixels having the same pixel characteristic into domains;

grouping domains containing pixels having the same pixel characteristic into groups of domains;

determining the surface occupied by each group of domains on the relatively regular surface;

selecting a portion of the scanned surface that includes at least one domain from each group of domains;

determining a measurement matrix having equidistant measurement sites covering the selected portion of the scanned surface;

taking measurements, using LIBS, at every measurement site;

determining, for each group of domains, the concentration of the constituent element in the group of domains by considering the LIBS measurements taken in measurement sites belonging to the group of domains;

determining a total quantity of constituent element of each group of domains; and, determining a concentration of the constituent element of the sample by dividing an added total quantity of the constituent element of each group of domains by a volume of the sample.

6. The concentration measurement method of claim 5 wherein the determination of the concentration of the constituent element in a particular group of domains includes averaging the LIBS measurements taken at measurement sites belonging to the particular group of domains.

7. The concentration measurement method of claim 5, wherein the distance between the equidistant measurement sites is slightly smaller than the smallest of the domains.

8. The concentration measurement method of claim 5, wherein the concentration of the constituent element in a group of domains is determined by:

$$Concentration_{Group} = \frac{\sum_{Domains}(Volume_{Domain} \times Concentration_{Domain})}{Volume_{Group}}$$

where $Volume_{Domain} = Surface_{Domain} * \sigma$ and $Volume_{Group} = Surface_{Group} * \sigma$ $\sigma$ being a predetermined thickness so determined that the boundary of each domain are assumed perpendicular to the relatively regular surface of the sample.

9. The concentration measurement method of claim 8, wherein the concentration of the constituent element in the sample is determined by:

$$Concentration_{Sample} = \frac{\sum_{Group}(Volume_{Group} \times Concentration_{Group})}{Volume_{Sample}}$$

where $Volume_{Sample} = Surface_{Sample} * \sigma$.

10. A method for measuring the concentration of a constituent element in an inhomogeneous sample having a relatively regular surface, the method comprising:

determining a number, size and position of domains on the relatively regular surface;

determining a surface occupied by each domain on the relatively regular surface; and, for each domain, measuring, using LIBS, the concentration of the constituent element in at least one measurement site of the domain;

determining a total quantity of constituent element of each domain; and, determining the concentration of the constituent element of the sample by dividing an added total quantity of the constituent element of each domain by a volume of the sample.

11. The concentration measurement method of claim 10, wherein the concentration of the constituent element in the sample is determined by:

$$Concentration_{Sample} = \frac{\sum_{Domains}(Volume_{Domain} \times Concentration_{Domain})}{Volume_{Sample}}$$

where $Volume_{Sample} = Surface_{Sample} * \sigma$ $Volume_{Domain} = Surface_{Domain} * \sigma$ $\sigma$ being a thickness so determined that the boundary of each domain are may be assumed perpendicular to the relatively regular surface of the sample.

12. A system for measuring the concentration of a constituent element in an inhomogeneous sample having a relatively regular surface, the system comprising:

a controller;

a three-axis positioning assembly configured to hold the sample and controlled by the controller;

a pulsed laser generally aimed at the relatively regular surface of the sample and controlled by the controller;

a camera generally aimed at the relatively regular surface of the sample and configured to supply a scanned image of at least a portion of the relatively regular surface to the controller;

a plasma emission collection assembly configured to collect light generated by a plasma on the relatively regular surface of the sample;

a spectrometer having an input configured to receive the light collected by the plasma emission collection assembly; the spectrometer having an output and being controlled by the controller;

an iCCD camera so mounted to the output of the spectrometer as to receive an image therefrom and supply the image to the controller;

wherein the controller may control the three-axis positioning assembly to place a desired measurement site at the aimed position of the pulse laser, control the pulsed laser as to generate a laser pulse that generates a plasma at the desired measurement site, receive the spectrum from the iCCD camera and determine the concentration of the constituent element from the received spectrum and the controller being further configured as to make such measurements at predetermined measurement sites determined by examination of the scanned image and to calculate the total concentration of the constituent element from the determined concentrations of the constituent element at the predetermined measurement sites.

13. A concentration measuring system as recited in claim 12 wherein the controller is a computer provided with an input device and a display.

14. A concentration measuring system as recited in claim 12, further including a second camera aimed at the relatively regular surface of the sample, the second camera being so configured as to supply an image of the aimed position of the pulse laser to ensure that the aimed position registers with the desired measurement site.

15. A concentration measuring system as recited in claim 14, further comprising a 50/50 beamsplitter to allow both cameras to aim at the same position on the relatively regular surface of the sample.

16. A concentration measuring system as recited in claim 12 wherein the pulse laser is selected from the group consisting of short pulse lasers and ultrashort pulse lasers.

17. A concentration measuring system as recited in claim 12, wherein the pulse laser is so controlled as to emit two pulse with a predetermined delay therebetween.

18. A concentration measuring system as recited in claim 12, wherein the three-axis positioning assembly is so configured as to define an enclosed space where an argon atmosphere may be maintained.

19. A concentration measuring system as recited in claim 12, wherein the three-axis positioning assembly is so configured as to define an enclosed space where a low pressure atmosphere may be maintained.

20. A concentration measuring system as recited in claim 12, wherein the plasma emission collection assembly includes first and second parabolic mirrors and a fiber optic provided with proximate and distal ends; the first parabolic mirror being so configured and positioned as to collect plasma light from the surface of the sample and the second mirror being so configured and positioned as to supply the collected plasma light to the proximate end of the fiber optic; the distal end of the fiber optic being connected to the input of the spectrometer to supply the collected plasma light thereto.

21. A concentration measuring system as recited in claim 20, wherein the optic fiber is a UV/VIS optic fiber.

22. A concentration measuring system as recited in claim 20, wherein the plasma emission collection assembly further includes a three-axis positioning assembly controlled by the controller.

23. A concentration measuring system as recited in claim 12, wherein the spectrometer is an Echelle spectrometer.

24. A concentration measuring system as recited in claim 14, further comprising a third camera aimed at the relatively regular surface of the sample to supply plasma information to the controller.

* * * * *